United States Patent [19]

Kawaguchi

[11] Patent Number: 5,064,369
[45] Date of Patent: Nov. 12, 1991

[54] ORTHODONTIC DEVICE

[75] Inventor: Kozo Kawaguchi, Futaba, Japan

[73] Assignee: Tomy, Inc., Ohkuma, Japan

[21] Appl. No.: 7,018

[22] Filed: Jan. 27, 1987

[51] Int. Cl.$^5$ .............................................. A61C 3/00
[52] U.S. Cl. ........................................... 433/3; 433/8
[58] Field of Search ................... 433/8, 9, 10, 11, 12, 433/17, 3

[56] References Cited

U.S. PATENT DOCUMENTS

| | | | |
|---|---|---|---|
| 1,976,141 | 10/1934 | Richardson | 433/8 |
| 2,045,025 | 6/1936 | Richardson | 433/8 |
| 2,926,422 | 3/1960 | Wallshein | 433/8 |
| 2,971,110 | 8/1959 | Schmidt . | |
| 3,026,177 | 3/1962 | Pierre et al. | 423/625 |
| 3,026,210 | 3/1962 | Coble | 501/153 |
| 3,181,240 | 5/1965 | Kerhart et al. | 433/203.1 |
| 3,207,937 | 5/1960 | Hannam . | |
| 3,256,602 | 6/1966 | Broussard et al. | 433/13 |
| 3,379,566 | 4/1968 | Hannam . | |
| 3,423,833 | 1/1969 | Pearlman | 433/8 |
| 3,464,837 | 9/1969 | McLean et al. | 433/202.1 |
| 3,496,637 | 2/1970 | Etengoff | 433/8 |
| 3,541,688 | 11/1970 | McLean et al. | 427/2 |
| 3,732,087 | 5/1973 | Grossman | 65/33 |
| 3,930,311 | 1/1976 | Andrews | 433/8 |
| 4,047,067 | 9/1977 | Clausen . | |
| 4,097,935 | 7/1978 | Jarcho | 423/633 |
| 4,197,118 | 4/1980 | Wiech, Jr. | 264/63 |
| 4,216,583 | 8/1980 | Reynolds | 433/9 |
| 4,219,617 | 8/1980 | Wallshein | 433/8 |
| 4,281,991 | 8/1981 | Michl et al. | 433/202.1 |
| 4,285,732 | 8/1981 | Charles et al. . | |
| 4,288,221 | 9/1981 | Engel | 433/202.1 |
| 4,302,532 | 11/1981 | Wallshein | 433/8 |
| 4,310,306 | 1/1982 | Wallshein | 433/9 |
| 4,321,042 | 3/1982 | Scheicher | 433/201.1 |
| 4,322,206 | 3/1982 | Reynolds | 433/9 |
| 4,364,731 | 12/1982 | Norling et al. | 433/218 |
| 4,381,918 | 5/1983 | Ehrnford | 433/202.1 |
| 4,388,069 | 6/1983 | Orlowski | 433/201.1 |
| 4,392,828 | 7/1983 | Ehrnford | 433/201.1 |
| 4,411,625 | 10/1983 | Koblitz et al. | 433/217.1 |
| 4,418,025 | 11/1983 | Prochazka et al. | 264/1.2 |
| 4,431,420 | 2/1984 | Adair | 433/202.1 |
| 4,431,421 | 2/1984 | Kawahara et al. | 433/202.1 |
| 4,460,336 | 7/1984 | Smith et al. | 433/9 |
| 4,523,908 | 6/1985 | Drisaldi et al. | 433/8 |
| 4,544,359 | 10/1985 | Waknine | 433/202.1 |
| 4,567,396 | 1/1986 | McVey . | |
| 4,595,598 | 6/1986 | DeLuca et al. | 427/2 |
| 4,626,208 | 12/1986 | Hall | 433/3 |
| 4,639,218 | 1/1987 | Jones et al. | 433/8 |
| 4,954,080 | 9/1990 | Kelly et al. | 433/8 |

FOREIGN PATENT DOCUMENTS

| | | |
|---|---|---|
| 3035829 | 6/1981 | Fed. Rep. of Germany ........ 433/13 |
| 1228754 | 11/1966 | Germany . |
| 1083769 | 9/1967 | U.K. . |
| 1541219 | 6/1970 | Germany . |
| 2039226 | 3/1971 | Germany . |
| 2554145 | 6/1977 | Germany . |
| 2913509 | 2/1980 | Germany . |
| 099741 | 1/1984 | Europe . |
| 160481 | 11/1985 | Europe . |
| 161831 | 11/1985 | Europe . |

OTHER PUBLICATIONS

The American Illustrated Medical Dictionary, p. 1447.
The American Heritage Dictionary, p. 571.
Some Optical, Thermo-Optical, and Piezo-Optical Properties of Synthetic Sapphire, M.A. Jeppesen, Journal of the Optical Society of America, vol. 48, No. 9, Sep. 1958, pp. 629 to 632.
Refraction and Dispersion of Synthetic Sapphire, I.H. Malitson, Journal of the Optical Society of America., vol. 52, No. 12, Dec., 1962, pp. 1377 to 1379.
Hot-Working of Alumnium Oxide: II, Optical Properties, W.H. Rhode, et al., Journal of the American Ceramic Society, vol. 58, No. 1-2, pp. 31 to 34.

Primary Examiner—Cary E. Stone
Attorney, Agent, or Firm—Kenyon & Kenyon

[57] ABSTRACT

An orthodontic device comprises a bracket formed of a sintered polycrystal of alumina exhibiting light transmittance of 70 to 80% and an auxilliary bonding member formed of a soft, transparent or translucent, thin, synthetic resin plate having a mounting aperture formed therein for mounting the bracket therein and a plurality of graduations drawn thereon for indicating the depth from a reference point on the free end of a tooth being subjected to orthodontic treatment to the center of the bracket.

20 Claims, 6 Drawing Sheets

ORTHODONTIC DEVICE

BACKGROUND OF THE INVENTION

The present invention relates to an orthodontic device adapted in the field of orthodontics for moving teeth in a prescribed direction for the purpose of correcting irregularities of the teeth, and more particularly to a novel orthodontic bracket.

Generally, orthodontic treatment for moving specified teeth in a prescribed direction is carried out by attaching a bracket firmly to the surface of a tooth being subjected to the orthodontic treatment; retaining an arch wire on the bracket through a ligature; and exerting a corrective force onto the tooth resulting from the bending and tension of the arch wire.

Brackets which have heretofore been used for this purpose generally are made of metal such as stainless steel because such materials satisfy the requirements indispensable to such brackets primarily a mechanical strength high enough to retain an arch wire thereon and physiological inactivity. The appearance of such brackets is a distinct disadvantage, however, as the patient's teeth exhibit a metallic appearance. This drawback has resulted in a search for a bracket that combines the strength of metallic brackets with a more pleasing appearance.

Japanese Patent Public Disclosure No. 60-234656 discloses a bracket formed of a single transparent crystal of monocrystalline alumina. Although this bracket has been proposed as a solution to the esthetic problems encountered by metallic brackets, it also presents several inherent drawbacks. First, this bracket is expensive to produce. The bracket is formed by pulling molten alumina within a crucible made of an expensive material such as iridium, platinum, etc., onto the upper surface of a die made of an similarly expensive material such as iridium, molybdenum, etc.; allowing the molten alumina on the die to grow into an alumina rod; cutting the alumina rod into pieces of a prescribed size; and subjecting each of the alumina pieces to secondary mechanical processing such as machining the bottom surface of the bracket so that it can be bonded to the curved tooth surface.

Not only does the crystal pulling process (known as the Czochralski Process) require the use of expensive equipment, it also entails limited productivity. The velocity of crystal growth into an alumina rod is very slow, inherently precluding a mass production process. Furthermore, the requirement for secondary mechanical processing introduces a number of cumbersome manufacturing steps.

Additionally, this device solves the esthetic problems of metallic brackets, but it introduces a new esthetic drawback of its own. Monocrystalline alumina is a simple crystal having no grain boundary, and it exhibits light transmittance of substantially 100%. When a bracket made of such monocrystalline alumina is mounted on a tooth, the bracket acts as a lens, and the color of the patient's own tooth becomes conspicuous through the transparent bracket when the patient opens his mouth, an appearance often found unpleasant. Thus, a completely transparent bracket does not always enhance the bracket's esthetic qualities, and therefore brackets formed of monocrystalline alumina have not yet gained widespread acceptance.

In addition, the monocrystalline alumina bracket is difficult to install. A metallic bracket is fixed to the surface of a tooth by welding a base member of a comparatively wide area such as wire gauze to the bottom surface of the metallic bracket and then applying a bonding material to the base member. Due to the material involved, one cannot weld such base members to monocrystalline alumina brackets, and therefore such brackets are bonded directly onto the tooth surface. On fixing the monocrystalline alumina bracket to the surface of a tooth, however, the bonding material applied to the bottom surface of the bracket flows outward to the rear side of wings formed on the opposite sides of the bracket and solidifies there. Because the rear sides of the bracket wings define spaces for stopping a ligature, the outflow of bonding material obstructs the installation of the ligature, requiring the orthodontist to remove such material. The necessity of this cumbersome step further militates against the practical use of transparent brackets of monocrystalline alumina.

Thus, the only alternative to metallic brackets offered by the prior art is expensive to manufacture, unpleasant in appearance, and difficult to install. Clearly, a need exists for a non-metallic bracket, pleasing in appearance, that can be produced rapidly and cheaply.

SUMMARY OF THE INVENTION

It is an object of the present invention to provide an orthodontic device capable of completely solving the problems encountered by conventional transparent brackets formed of monocrystalline alumina and also capable of being advantageously put to practical use from the standpoints of economy, esthetic appreciation and ease of installation.

These and other objects are achieved by the present invention, in which an orthodontic device comprises bracket means for engaging an arch wire therein, having a longitudinal slot formed in a central upper surface thereof. The bracket is formed of a sintered polycrystal of alumina, and it further includes wing means for stopping a ligature thereon, carried integrally on opposite sides of the bracket. Auxiliary bonding member means are molded separately from the bracket the auxiliary bonding member being formed of a soft, transparent, thin plate, having a mounting aperture formed therein for detachably mounting the bracket therein, and also having a graduations thereon for indicating a depth between a reference point on the free end of a tooth being subjected to orthodontic treatment and the center of the bracket.

Further, according to the present invention, the bracket is formed of a sintered polycrystal of alumina having light transmittance of 70 to 80%, thereby eliminating the unpleasant esthetic appearance of the conventional monocrystalline alumina having 100% light transmittance and enhancing color harmony between the bracket and a patient's own

DETAILED DESCRIPTION OF A PREFERRED EMBODIMENT

Figure 1:
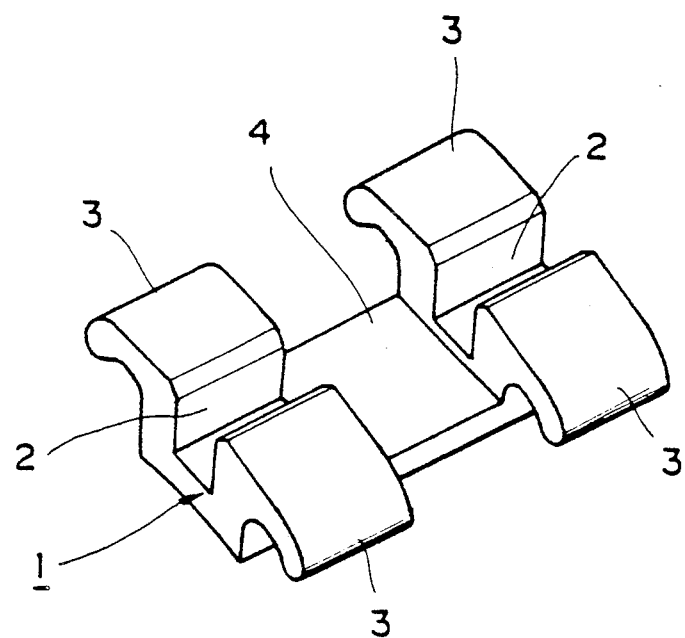
FIG. 1 is a pictorial illustration of a conventional bracket of monocrystalline alumina.

FIG. 1 shows a conventional bracket of monocrystalline alumina, which is formed by preparing a bracket body 1, forming a U-shaped slot 2 for engaging an arch wire therein in the upper central portion of the bracket body, forming wings 3 integrally on the opposite sides of the bracket body 1 for stopping a ligature thereon, and cutting the entire central portion off the bracket body 1 in the lateral direction to form an intermediate portion 4 which divides the U-shaped slot 2 and each of the wings 3 respectively into two portions in the longitudinal direction. Further, the bottom surface of the bracket body 1 is formed in a shape conforming to a curved surface of a tooth.

In the method for manufacturing the conventional bracket, molten alumina is pulled up from a crucible onto a die and allowed to grow into an alumina rod by the Czochralski Process as described above. The alumina rod is cut into pieces of a prescribed size, and each of the alumina pieces is subjected to cumbersome secondary mechanical processing including cutting, grinding and polishing to form the U-shaped slot 2, intermediate portion 4 and the curved bottom of the bracket Because the Czochralski Process requires expensive equipment and entails slow crystal growth, manufacturing costs are high. The necessity for secondary processing steps further increases the manufacturing cost of such brackets. Furthermore, the formation of the intermediate portion 4 on the bracket body 1 not only requires a processing step, but also that step cuts the U-shaped slot 2 into two longitudinal portions, making retention of an arch wire (not shown) therein unstable Worse, this step lowers the strength of the entire bracket, posing a structural problem.

Because monocrystalline alumina is a simple crystal having no grain boundaries, monocrystalline alumina has substantially 100% light transmittance. Consequently, the color of a patient's own tooth becomes conspicuous through the transparent bracket when the patient opens his mouth, presenting an unpleasant appearance. Thus the esthetic problem associated with metallic brackets has been replaced with a new drawback.

Figure 2:
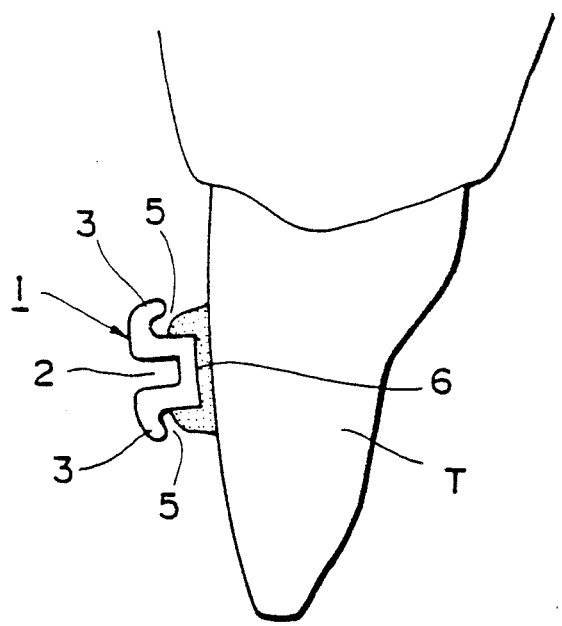
FIG. 2 is a side view illustrating the conventional bracket of FIG. 1 as attached to the surface of a tooth.

In actual orthodontic treatment using the bracket of monocrystalline alumina, a bonding material 6 is applied directly to the bottom surface of the bracket body 1, and the bracket body 1 is fixed to the surface of a tooth T, as illustrated in FIG. 2. During that bonding, however, the bonding material 6 applied to the bottom surface of the bracket body will extend to the rear sides of the wings 3 formed on the opposite sides of the bracket body and will solidify there. The rear sides of the wings 3 define spaces 5 for stopping a ligature (not shown) therein, and the solidified bonding material under the wings fills the spaces 5 and prevents the ligature from being stopped therein. Therefore, the cumbersome task of eliminating the solidified bonding material must be separately effected after fixing the bracket body to the surface of the tooth. Thus, the bracket of monocrystalline alumina presents a disadvantage from the standpoint of orthodontic treatment.

Figure 3A:
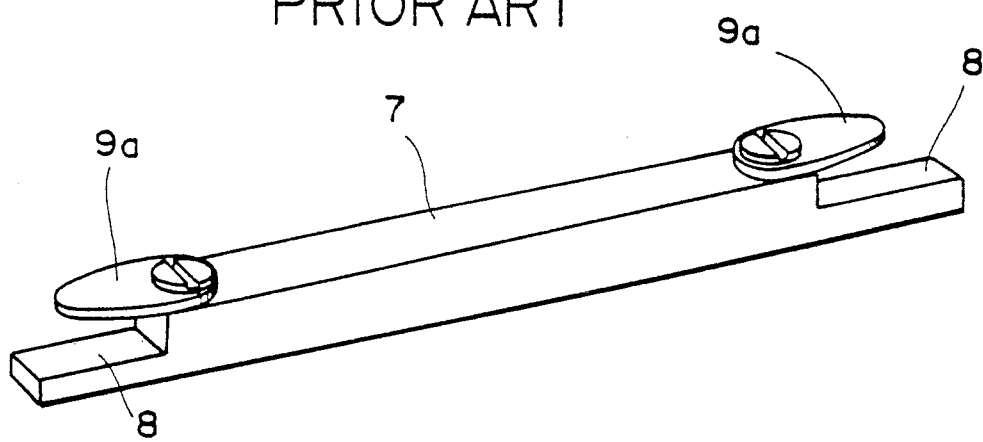
FIG. 3A is a pictorial illustrating a first conventional bracket positioning gauge.
Figure 3B:
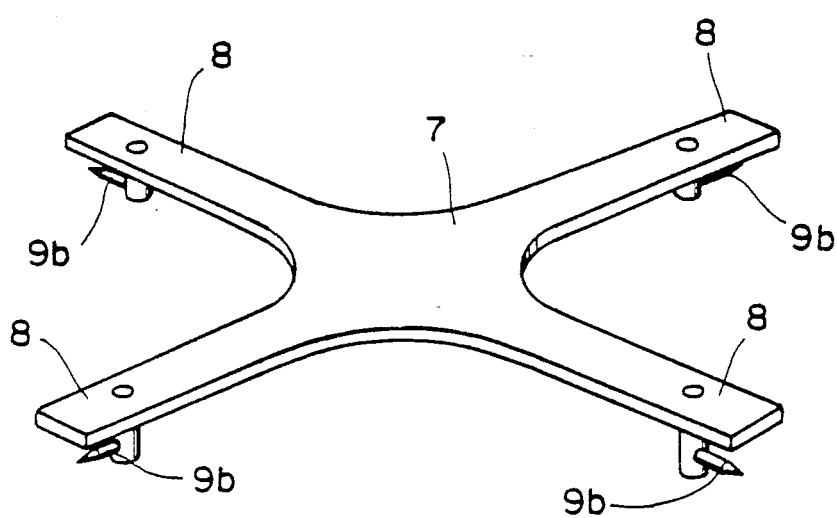
FIG. 3B is a perspective illustrating a second conventional bracket positioning gauge.

Inasmuch as the purpose of an orthodontic bracket is to transmit a load from an arch wire retained in a bracket slot to a tooth subjected to orthodontic treatment, the bracket must be attached to the tooth at an optimum position. Conventional brackets, however (both those of metal and those of monocrystalline alumina), are not provided with any means or structure capable of indicating the optimum position of the bracket on the tooth surface. To solve this problem, the art teaches the use of a bracket positioning gauge in attaching the bracket. Two such gauges known to the art are shown in FIGS. 3A and 3B. As shown, the gauge comprises a gauge body 7 formed in the shape of a rod or a cross, ruler sections 8 formed on the free ends of the gauge body 7, and indication plates 9a or indication pins 9b fixed to the gauge body 7 facing the ruler sections 8 at stepwise different prescribed distances from same. In use, the orthodontist grasps the gauge body 7, and one of the ruler sections 8 is brought into intimate contact with a reference point at the free end of the tooth, specifically the incisal of an incisor, the cuspidate ledge of a cuspid or the cusp of a molar or bicuspid. The leading end of a corresponding indication plate 9a or indication pin 9b then indicates the position on the tooth at which the bracket is to be fixed.

Because the conventional bracket positioning gauge has only two or four pairs of indication plates or pins and ruler sections, it thus can present only two or four different distances between an indication plate or pin and the ruler section. Thus, such devices cannot always precisely indicate an optimum position of a bracket relative to a tooth, which position varies depending on the kind and size of the tooth and also upon any irregularities of the tooth. Further, use of the bracket positioning gauge requires that the operations of choosing an optimum position that attaching the bracket body be carried out independently. Such steps increase the time and effort of orthodontic treatment.

The present invention removes the various disadvantages and drawbacks described above, and an embodiment of the invention is illustrated in FIGS. 4-8. The illustrated embodiment of the orthodontic device according to the present invention comprises a bracket for retaining an arch wire and an auxiliary member molded separately from the bracket, and is characterized by the use of the bracket and the auxiliary bonding member in mutual cooperation to effect orthodontic treatment.

Figure 4:
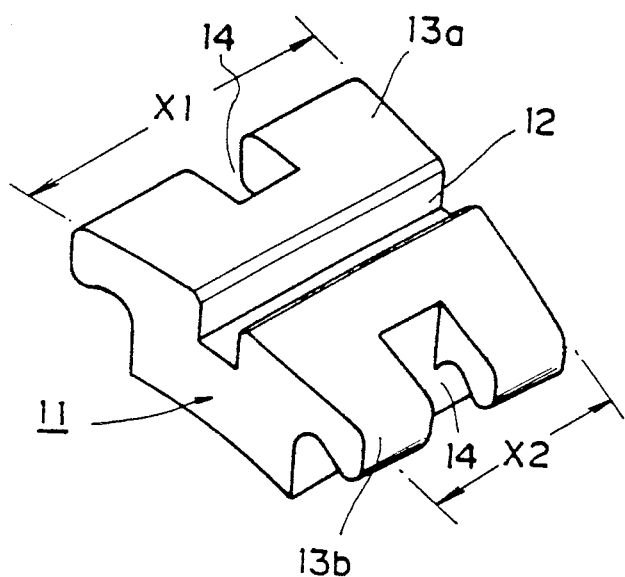
FIG. 4 is a pictorial representation of one embodiment of a bracket of polycrystal alumina according to the present invention.
Figure 5:
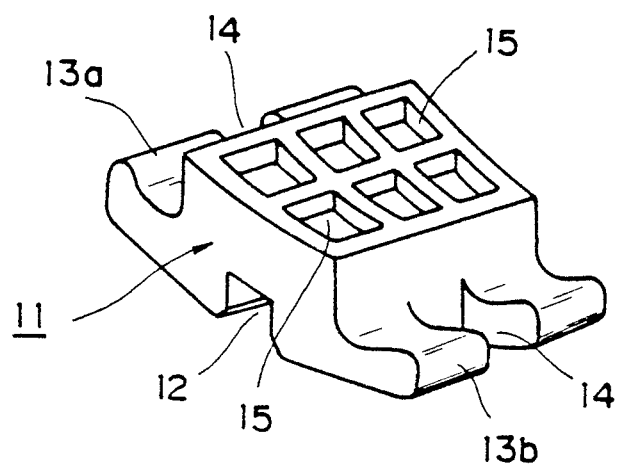
FIG. 5 is a pictorial representation of the embodiment of FIG. 4, as seen from the bottom.

FIGS. 4 and 5 illustrate one embodiment of the bracket as one part of the orthodontic device according to the present invention. The bracket comprises a bracket body 11 having a longitudinal U-shaped slot 12 formed in the upper central surface thereof for engaging an arch wire (not shown) therein, and a pair of wings 13a and 13b integral to the bracket and laterally projecting from the upper opposite sides of the bracket body 11 for stopping thereon a ligature (not shown). For purposes of reference, the term "upper" as used herein refers to the surface shown projecting toward the reader in FIG. 4, which surface forms the buccal portion of the bracket. The width X1 of one of the wings 13a is set larger than the width X2 of the other wing 13b. Each of the wings 13a and 13b has a cut portion 14 formed in the center thereof extending toward but not intersecting the U-shaped slot 12

It should be noted that the slot 12 is continuous over the entire width of the bracket body, with no intermediate cutout portion such as the area 4 seen in the conventional bracket of FIG. 1. This continuous slot permits firm engagement of the arch wire across the width of the bracket. Further, the differing widths X1 and X2 of the wings 13a and 13b facilitate the task of stopping a ligature on the wings Those in the art will understand, of course, that the widths X1 and X2 of the wings may be provided equal to each other as desired.

The bottom surface of the bracket body 11 of the present invention is curved so as to conform to the surfaces of a tooth, as illustrated in FIG. 5. To promote adhesion while preventing the outflow of bonding material, the bracket is provided with a plurality of recesses 15 for allowing entry of excess bonding material In order to enhance the strength of adhesion, the walls defining the recesses 15 may be corrugated as occasion demands.

The bracket of the present invention preferably is formed of a sintered polycrystal of alumina A raw material for the sintered polycrystalline alumina bracket is prepared by adding a minute amount of magnesia (as further detailed below) and other known additives to a principal component of powdered alumina having high purity, and sufficiently stirring and pulverizing the resultant mixture. To the raw material thus prepared, a suitable amount of an organic binder such as. for example, polyvinyl alcohol, is added. The resultant mixture is subjected to drying, such as with a spray drier, and to size enlargement, thereby obtaining particles suitable for molding The particles may be molded by a dry press molding machine or other suitable apparatus, using a mold designed to produce the bracket body 11. The molding is then subjected to preliminary sintering at temperatures in the range of 1000° to 1300° C. in the atmosphere, thereby removing the organic binder, and then to finishing sintering at temperatures in the range of 1700° to 1800 C. under vacuum, thereby obtaining a sintered polycrystalline alumina bracket excellent in mechanical strength. Those skilled in the art will understand the known process of preparing and molding as described above, and further detail of such process is not required herein.

The bracket of sintered polycrystal alumina can thus be manufactured readily and inexpensively. Utilization of a molding process eliminates the necessity for cumbersome secondary processing steps required by the prior art. According to the present invention, therefore, the steps of manufacturing a bracket can be greatly reduced as compared with the prior art.

Further, the present invention eliminates the unpleasant esthetic appearance of the conventional monocrystalline alumina bracket. It has been found that the polycrystal of the present invention exhibits a light transmittance in the range of 70 to 80%. This transmittance level matches that of the enamel surface of a tooth, and thus the color of the bracket matches well with the color of the tooth.

The desirable light transmittance of the present invention is obtained in the following manner. As is known to the art, addition of an optimum amount of magnesia effectively suppresses the growth of an alumina crystal to increase transparency. It is also well known that when the amount of magnesia exceeds the optimum amount, spinel ($MgAl_2O_4$) is increasingly produced. The refractive index of spinel being greatly different from that of alumina, the spinel refracts light and thus lowers the light transmittance.

The lowered light transmittance of the present invention, in the range of 70 to 80%, is obtained by utilizing the characteristics of magnesia described above. To be specific, the amount of magnesia added is slightly increased as compared with the optimum amount, which varies depending on the manufacturing conditions. Those in the art will understand the methods used for determining the optimum amount, and the simple experimentation required to establish the precise amount by which the magnesia should exceed that optimum amount to achieve the light transmittance range desired. In addition, other means could be used to establish this lowered transmittance. For example, the light transmittance can be adjusted to 70 to 80% by changing the relation between the sintering temperature and the sintering time.

Figure 6:
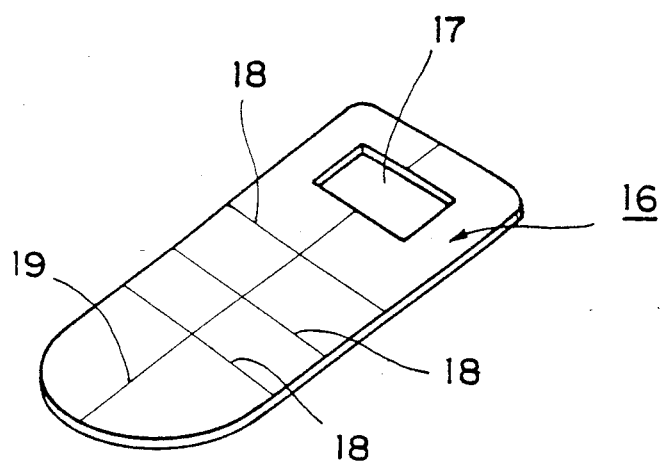
FIG. 6 is a perspective illustrating one embodiment of an auxiliary bonding member according to the present invention.

FIG. 6 illustrates one embodiment of the auxiliary bonding means as the other part of the orthodontic device of the present invention, used in conjunction with the bracket body 11. The auxiliary bonding member 16 is a thin plate of a soft, transparent or translucent synthetic resin material preferably having a rectangular shape with one end rounded off. A mounting aperture 17, dimensioned to accept the lower portion of the bracket body, is formed in one end of the member, and a tooth center confirmation line 19 is inscribed on the long axis of the plate. A plurality of graduations 18 is drawn on the plate surface, parallel to the short axis of the plate, for indicating the depth from a reference point on a tooth to the center of the bracket body 11. The mounting aperture 17 is substantially the same in shape and size as the bottom surface of the bracket body, so that the bracket body can be mounted in the aperture with precision. The pitch of the graduations 18 may suitably be selected. Preferably, however, the graduations are spaced in millimeters.

Figure 7:
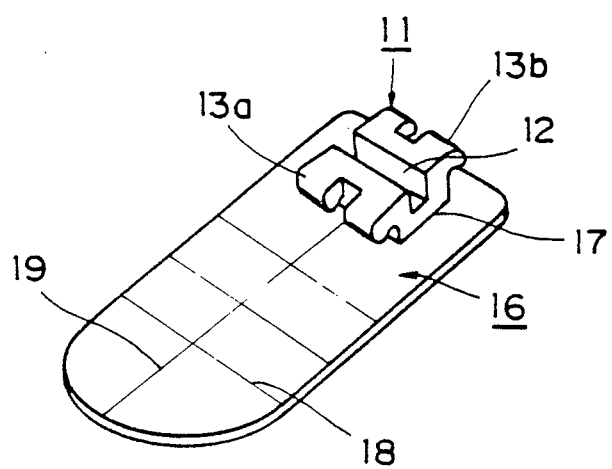
FIG. 7 is a pictorial representation of the auxiliary bonding member of FIG. 6 having the bracket of FIG. 4 mounted in a mounting aperture thereof.

The process of fixing the bracket onto the surface of a tooth begins by inserting the bracket body into the mounting aperture, utilizing the resiliency of the member 16 to enlarge the aperture 17, as illustrated in FIG. 7, so that the rear sides of the wings 13a and 13b of the bracket body 11 are disposed at a given interval from the surface of the member In this state, the space for stopping a ligature can sufficiently be secured between the upper surface of the auxiliary bonding member and the lower surface of the wings 13a and 13b of the bracket body.

Figure 8A:
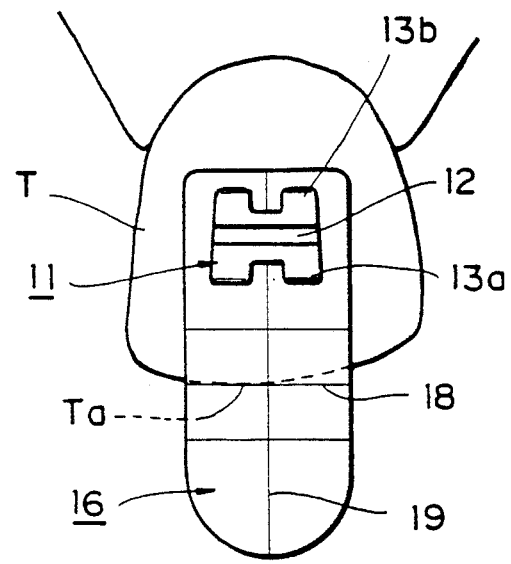
FIG. 8A is a front view illustrating the bracket as attached to the surface of a tooth with the auxiliary bonding member.
Figure 8B:
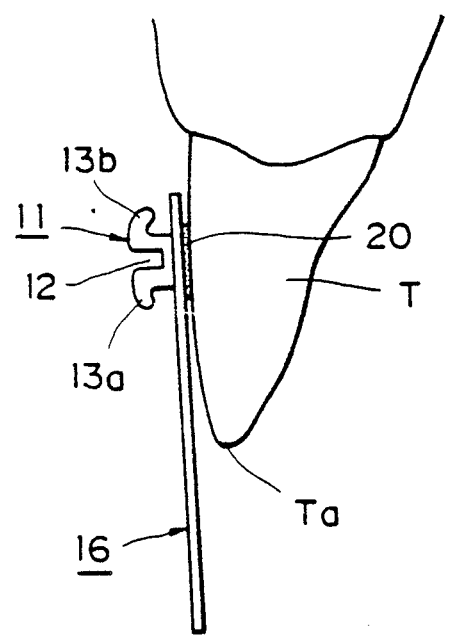
FIG. 8B is a side view illustrating the bracket as seen in FIG. 8A.

In the state described above, a bonding material 20 is applied to the bottom surface the bracket body. The bracket body is picked up with a pincette or the like (not shown) at a suitable place and is moved suitably longitudinally and/or laterally with respect to the surface of tooth T (as shown in FIGS. 8A and 8B) until a preselected graduation 18 on the auxiliary bonding member is aligned with a reference point Ta of the leading end of the tooth T, specifically the incisal of an incisor, the cuspidate ledge of a cuspid or the cusp of a molar or bicuspid. Upon confirmation of alignment, the assembly is pressed against the surface of the tooth, fixing the bracket body to the tooth surface at an optimum position, as illustrated in FIG. 8B, in accordance with the needs of individual orthodontic treatment. As the auxiliary bonding member 16 is transparent or translucent, it is relatively easy to confirm through the member 16 whether a given graduation 18 is in alignment with the reference point Ta of the tooth, by making use of the tooth center confirmation line 19 to center the member with respect to the surface of the tooth by visual inspection. Therefore, the bracket body 11 can rapidly be fixed to the tooth T precisely at the optimum position, thereby making it possible to enhance considerably the ease of orthodontic treatment.

Further, because the auxiliary bonding member is mounted on the lower portion of the bracket body when bonding is effected, any bonding material expelled from the bottom surface of the bracket body when pressing the bracket body against the tooth surface is blocked by the auxiliary bonding member and cannot extend to the rear sides of the wings. Therefore, there is no possibility of the spaces on the rear sides of the wings being clogged with solidified bonding material. Further, overflow of the bonding material can be prevented to some extent due to the presence of the recesses formed in the bottom surface of the bracket body and, therefore, there exists no problem of a great quantity of bonding material overflowing, as has heretofore been encountered.

After fixing the bracket body to the surface of the tooth, the auxiliary bonding member is removed from the bracket body by expanding the mounting aperture, again utilizing the flexibility of the auxiliary bonding member, thereby detaching the member 16 from the bracket body. Subsequently, an arch wire is retained within the slot 12 with a ligature (not shown). The orthodontic treatment can thus be carried out reliably and accurately. In addition, since the spaces on the rear sides of the wings are free from solidified bonding material, there is no need to remove such bonding material. Furthermore, the presence of the recesses filled with the bonding material enhances the attachment of the bracket body to the tooth surface.

Those skilled in the art will understand that changes and modifications in the embodiment described herein may be made without departing from the spirit of the invention. For example, though it has proved advantageous to configure the bracket with wings of differing widths, it may be desired to produce a bracket whose wings are substantially equal. These and other changes may be made within the scope of the invention, which is defined by the claims appended hereto.

I claim:

1. An orthodontic device comprising:
bracket means for engaging an arch wire therein, having a longitudinal slot formed in a central upper surface thereof,
said bracket means being formed of a sintered polycrystal of alumina, and
a plurality of wings carried integrally on opposite sides of said bracket; and
an auxiliary bonding member molded separately from said bracket, said auxiliary bonding member being formed of a soft, transparent, thin plate, having a mounting aperture formed therein for detachably mounting upon said bracket means, said bonding member having graduations thereon for indicating a depth between a reference point on the free end of a tooth being subjected to orthodontic treatment and the center of said bracket.

2. An orthodontic device according to claim 1, wherein said bracket is formed of a sintered polycrystal of alumina exhibiting light transmittance of 70 to 80%.

3. An orthodontic bracket having a body portion defining a longitudinal slot therein and laterally projecting wing portions integral therewith, said bracket being formed of a sintered polycrystal of alumina and a substance having a refractive index different from the refractive index of polycrystalline alumina, said substance being added in an amount sufficient such that the light transmittance of the polycrystal of alumina is of approximately 70 to 80%.

4. An orthodontic bracket according to claim 3 wherein said substance comprises spinel.

5. The orthodontic bracket of claim 3 wherein said substance having a refractive index different from the refractive index of polycrystalline alumina is magnesia, said magnesia being present in an amount slightly above an optimum amount in order to produce the light transmittance of approximately 70 to 80%.

6. The orthodontic bracket of claim 5 wherein the light transmittance of approximately 70 to 80% causes the bracket to match well with the color of the tooth.

7. A ceramic orthodontic bracket consisting essentially of sintered polycrystalline alumina and a small amount of magnesia, the sintered polycrystalline alumina having a light transmittance in the range of approximately 70 to 80%.

8. The ceramic orthodontic bracket of claim 7 wherein said bracket includes a base member for attaching said bracket to a tooth and a body member extending from said base member including walls defining an archwire groove, said base member including a plurality of apertures formed therein for receiving tooth bonding material for attaching said bracket to a tooth.

9. An orthodontic bracket comprising a base member for attaching said bracket to a tooth and a body member extending from said base member, said body member including walls defining an archwire groove, wherein said bracket consists essentially of a sintered polycrystalline alumina having a light transmittance in the range of approximately 70 to 80% to enhance color harmony between the bracket and tooth.

10. The orthodontic bracket of claim 9 wherein said sintered polycrystalline alumina includes a small amount of magnesia therein, the amount of magnesia having been selected in order to obtain the approximately 70 to 80% light transmittance.

11. The orthodontic bracket of claim 9 wherein said base member includes a surface intended for adhesive contact with a tooth and including a plurality of recesses formed therein for receiving adhesive material for enhancing the mechanical adhesion of said surface to a tooth.

12. An orthodontic bracket as defined in claim 9 wherein the approximately 70 to 80% light transmittance is obtained by adjusting the relation between the sintering temperature and the sintering time thereof.

13. An orthodontic appliance formed of a sintered polycrystal of alumina exhibiting a light transmittance in the range of approximately 70 to 80% in order to substantially match the color of a tooth.

14. An orthodontic appliance as defined in claim 13 comprising a bottom surface shaped to conform to a curved surface of a tooth and including a plurality of recesses formed therein for receiving adhesive material to bond the appliance to a tooth; a body portion forming a slot therein for receiving an archwire; and at least two wing portions located on opposite sides of the body portion relative to each other for stopping a ligature thereon.

15. An orthodontic appliance as defined in claim 13 further including a predetermined amount of magnesia, the predetermined amount having been selected in order to obtain the light transmittance in the range of approximately 70 to 80%.

16. An orthodontic appliance for mounting on a tooth consisting essentially of a polycrystal of alumina and a predetermined amount of magnesia added thereto, the polycrystal of alumina exhibiting a light transmittance in the range of approximately 70 to 80% to enhance the color harmony between the appliance and tooth, the predetermined amount of magnesia having been selected by determining the optimum amount of magnesia for suppressing the growth of the alumina crystal to increase transparency, and by increasing the optimum amount to obtain a predetermined amount which in turn causes the light transmittance to fall in the range of approximately 70 to 80%.

17. An orthodontic appliance as defined in claim 16, comprising a tooth-abutting surface shaped to substantially conform to the morphology of a tooth and including a plurality of recesses formed therein for receiving adhesive material to enhance the adhesion of the appliance to the tooth; a body portion defining a slot therein for receiving an archwire; and wing portions located on opposite sides of the body portion for wrapping ligature or elastics thereon.

18. An orthodontic device comprising:
an appliance for engaging an arch wire therein, said appliance being formed of a sintered polycrystal of alumina, and including a longitudinal slot formed in a central upper surface thereof, and a plurality of wings carried integrally on opposite sides thereof; and an auxiliary bonding member molded separately from said appliance, said auxiliary bonding member being formed of a plastic plate member including a mounting aperture formed therein for detachably mounting upon said appliance, said bonding member including means thereon for indicating a depth between any of a plurality of reference points and the center of said appliance for aligning said appliance on any of a plurality of teeth, each reference point being on the free end of a respective tooth being subjected to orthodontic treatment.

19. An orthodontic device as defined in claim 18, wherein said sintered polycrystal of alumina of said appliance exhibits a light transmittance in the range of approximately 70 to 80% in order to substantially match the color of a tooth.

20. An orthodontic device as defined in claim 19, wherein said plastic plate member is made of a flexible transparent or translucent plastic material and said means for indicating a depth includes graduations formed on said plastic plate member.

* * * * *

UNITED STATES PATENT AND TRADEMARK OFFICE
CERTIFICATE OF CORRECTION

PATENT NO. : 5,064,369
DATED : November 12, 1991
INVENTOR(S) : Kozo KAWAGUCHI It is certified that error appears in the above-identified patent and that said Letters Patent is hereby corrected as shown below:

Column 1, line 20, after "brackets" insert a comma.

Column 2, line 47, delete "a" between "having" and "graduations".

Column 2, line 57, after "own" insert --teeth.--

Column 4, line 47, change "that" to --and--.

Column 5, line 28, change "alumina A" to --alumina. A--

Column 5, line 39, change "molding The" to --molding. The--

Column 7, line 2, after "treatment.", "As" should start a new paragraph.

Signed and Sealed this

Thirtieth Day of March, 1993

*Attest:*

STEPHEN G. KUNIN

*Attesting Officer*  *Acting Commissioner of Patents and Trademarks*